United States Patent
Gall et al.

(10) Patent No.: US 10,022,233 B1
(45) Date of Patent: Jul. 17, 2018

(54) ORTHOPEDIC IMPLANT FOR SUSTAINED DRUG RELEASE

(71) Applicant: Duke University, Durham, NC (US)

(72) Inventors: Ken Gall, Durham, NC (US); Thorsten M. Seyler, Durham, NC (US); Brian Allen, Durham, NC (US); Sarah Dicker, Potomac, MD (US); Catherine Oliver, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 15/830,561

(22) Filed: Dec. 4, 2017

(51) Int. Cl.
*A61F 2/38* (2006.01)
*A61F 2/30* (2006.01)

(52) U.S. Cl.
CPC ............ *A61F 2/30771* (2013.01); *A61F 2/38* (2013.01); *A61F 2/389* (2013.01); *A61F 2/3859* (2013.01); *A61F 2002/30062* (2013.01); *A61F 2002/3068* (2013.01); *A61F 2002/3092* (2013.01)

(58) Field of Classification Search
CPC .. A61F 2/38; A61F 2/389; A61F 2002/30677; A61F 2002/30678; A61F 2002/3068; A61F 2/30742; A61F 2/28; A61F 2/36; A61B 17/56
See application file for complete search history.

(56) References Cited

U.S. PATENT DOCUMENTS

| | | | | |
|---|---|---|---|---|
| 6,942,475 B2 * | 9/2005 | Ensign | ................ | A61F 2/30942 249/55 |
| 7,090,668 B1 * | 8/2006 | U | ......................... | A61K 9/0024 604/892.1 |
| 7,637,729 B2 * | 12/2009 | Hartman | .................... | A61F 2/30 249/102 |
| 8,454,706 B2 * | 6/2013 | de Beaubien | ............. | A61F 2/36 623/23.39 |
| 8,900,323 B2 * | 12/2014 | de Beaubien | ............. | A61F 2/36 623/23.39 |
| 9,517,134 B2 | 12/2016 | Lang | | |
| 9,642,658 B2 | 5/2017 | Boyd et al. | | |
| 9,730,809 B2 | 8/2017 | Samuelson et al. | | |
| 9,839,523 B1 * | 12/2017 | Foran | ...................... | A61F 2/389 |
| 2002/0169507 A1 * | 11/2002 | Malone | ............. | A61B 17/7064 623/17.11 |
| 2003/0060891 A1 * | 3/2003 | Shah | .................... | A61F 2/30728 623/22.13 |
| 2003/0187513 A1 * | 10/2003 | Durniak | ............. | A61B 17/8802 623/22.12 |

(Continued)

*Primary Examiner* — Alvin Stewart
(74) *Attorney, Agent, or Firm* — Benesch, Friedlander, Coplan & Aronoff LLP

(57) ABSTRACT

An orthopedic implant device has a bone-replacement contour that replicates a healthy bone surface contour. An exterior surface of the device has elution pores. Interior surfaces of the device define a reservoir that is spaced inward from the exterior surface. The reservoir stores a therapeutic agent delivery medium impregnated with a therapeutic agent. The interior surfaces further define elution channels communicating the reservoir with the elution pores to convey a therapeutic agent from the reservoir to the exterior surface. A solid therapeutic agent delivery medium is stored in the reservoir, and is biodegradable under the influence of synovial fluid.

19 Claims, 3 Drawing Sheets

(56) References Cited

U.S. PATENT DOCUMENTS

| | | | |
|---|---|---|---|
| 2004/0054417 A1* | 3/2004 | Soffiati | A61F 2/38 623/20.31 |
| 2005/0015154 A1* | 1/2005 | Lindsey | A61B 17/68 623/23.46 |
| 2005/0049707 A1* | 3/2005 | Ferree | A61B 17/8811 623/17.13 |
| 2005/0154470 A1 | 7/2005 | Sekel | |
| 2006/0093646 A1* | 5/2006 | Cima | A61C 8/0012 424/425 |
| 2006/0155381 A1* | 7/2006 | Katzman | A61F 2/3662 623/22.12 |
| 2006/0155382 A1* | 7/2006 | Katzman | A61F 2/3662 623/23.15 |
| 2007/0005142 A1* | 1/2007 | Rhodes | A61F 2/389 623/20.32 |
| 2007/0016163 A1* | 1/2007 | Santini, Jr. | A61C 8/0012 604/500 |
| 2007/0116734 A1* | 5/2007 | Akash | A61F 2/30 424/423 |
| 2007/0203584 A1* | 8/2007 | Bandyopadhyay | A61F 2/28 623/23.5 |
| 2007/0213832 A1* | 9/2007 | Wen | A61F 2/4455 623/23.5 |
| 2008/0147187 A1* | 6/2008 | Bollinger | A61F 2/367 623/11.11 |
| 2009/0069899 A1* | 3/2009 | Klein | A61F 2/36 623/22.4 |
| 2009/0304775 A1* | 12/2009 | Joshi | A61F 2/30 424/426 |
| 2010/0042213 A1* | 2/2010 | Nebosky | A61B 17/56 623/16.11 |
| 2010/0042214 A1* | 2/2010 | Nebosky | A61B 17/56 623/16.11 |
| 2010/0042215 A1* | 2/2010 | Stalcup | A61B 17/68 623/16.11 |
| 2010/0217401 A1* | 8/2010 | de Beaubien | A61F 2/36 623/20.34 |
| 2011/0218644 A1* | 9/2011 | Meridew | A61F 2/3662 623/23.15 |
| 2014/0194811 A1* | 7/2014 | Barsoum | A61F 2/38 604/35 |
| 2015/0238691 A1* | 8/2015 | Boyden | A61F 2/30 604/66 |
| 2015/0250598 A1* | 9/2015 | Yakimicki | A61F 2/3859 623/20.35 |
| 2016/0166284 A1* | 6/2016 | Hacking | A61B 17/56 604/892.1 |
| 2016/0367371 A1* | 12/2016 | de Beaubien | A61F 2/3609 |
| 2017/0181799 A1 | 6/2017 | Bonutti | |
| 2017/0312088 A1* | 11/2017 | Grotz | A61L 27/54 |
| 2017/0348104 A1* | 12/2017 | Wei | A61L 27/425 |
| 2018/0021554 A1* | 1/2018 | Nebosky | A61M 31/002 |

* cited by examiner

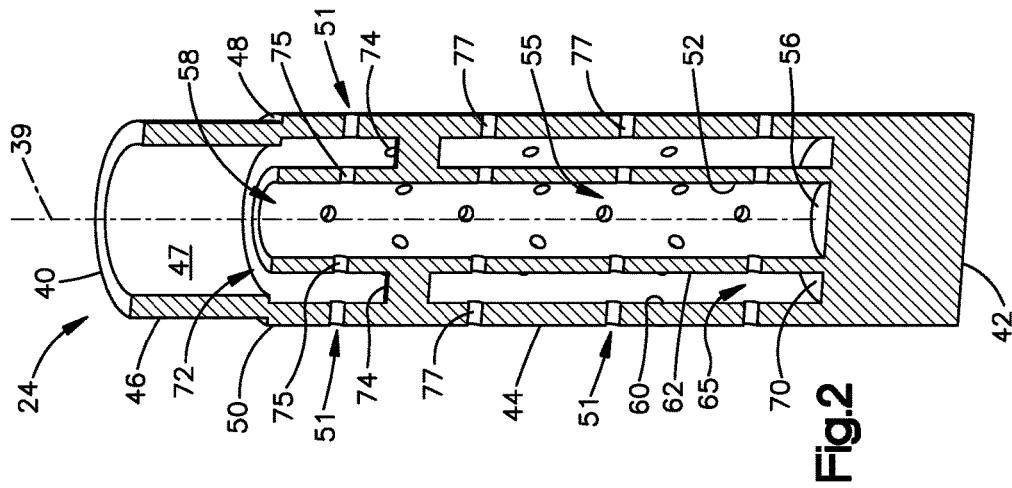
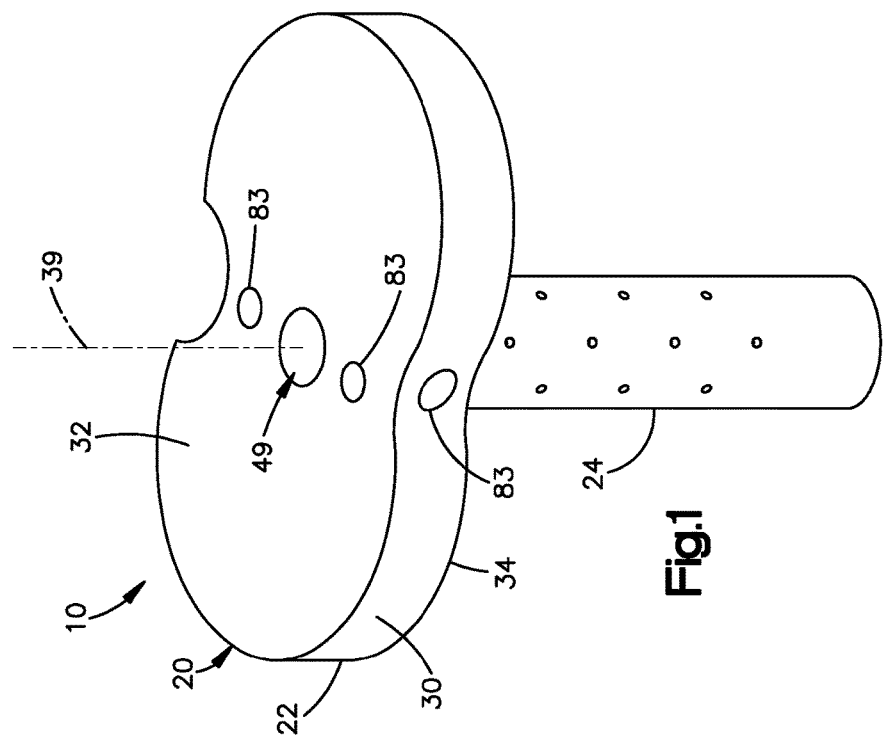

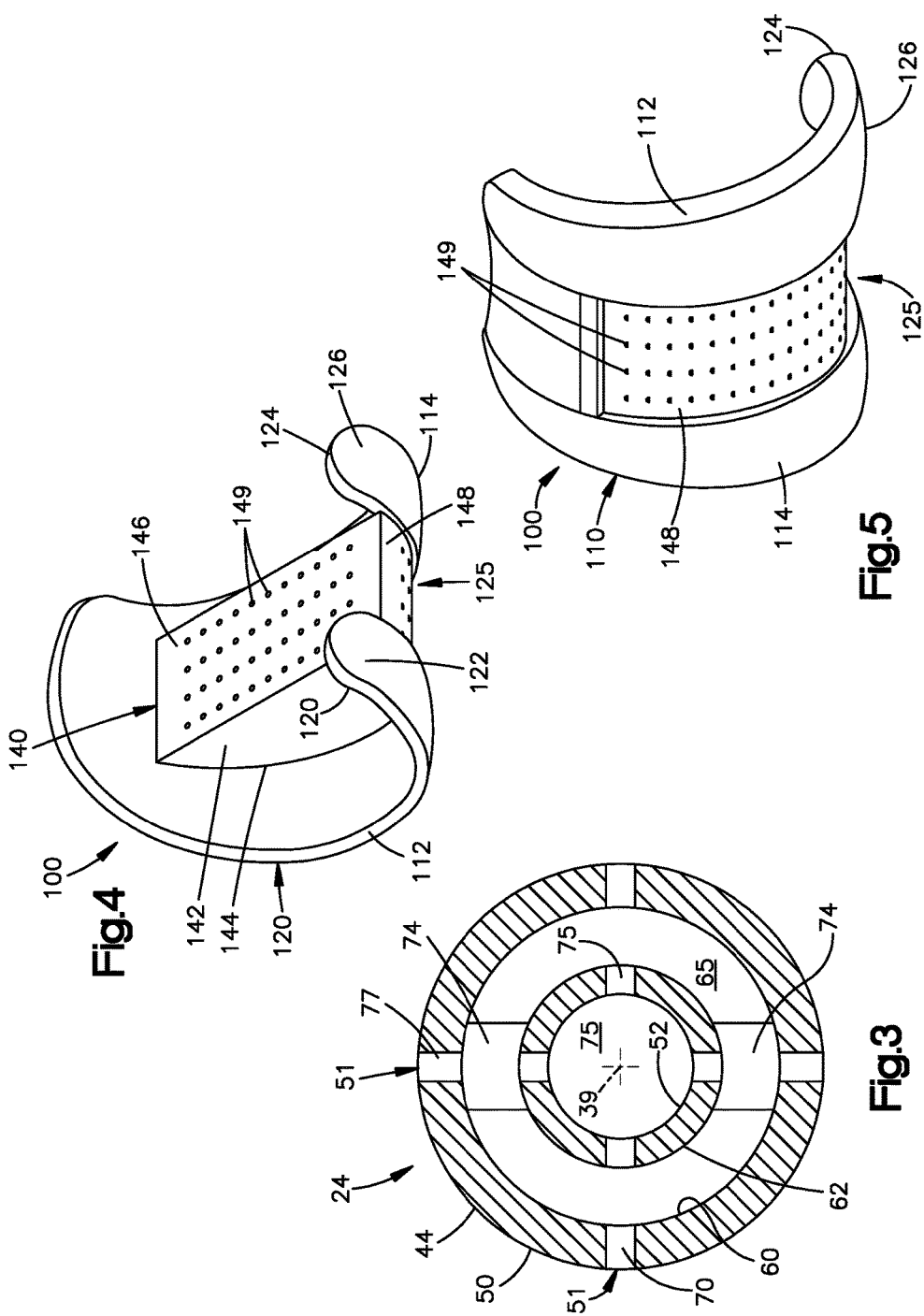

ORTHOPEDIC IMPLANT FOR SUSTAINED DRUG RELEASE

TECHNICAL FIELD

This technology relates to an implantable orthopedic device that provides for elution of a therapeutic agent.

BACKGROUND

An implantable orthopedic device, such as a component of a bone or joint replacement system, may contain an antibiotic or other therapeutic agent for elution from the device while the device is implanted.

SUMMARY

An orthopedic implant device has a bone-replacement contour that replicates a healthy bone surface contour. An exterior surface of the device has elution pores. Interior surfaces of the device define a reservoir that is spaced inward from the exterior surface. The reservoir is configured to store a solid therapeutic agent delivery medium impregnated with a therapeutic agent. The interior surfaces further define elution channels communicating the reservoir with the elution pores to convey a therapeutic agent from the reservoir to the exterior surface. A solid therapeutic agent delivery medium is stored in the reservoir, and is biodegradable under the influence of synovial fluid. This can sustain the elution of the therapeutic agent over a more extended period of time compared to the more rapid elution of a liquid in the absence of a solid biodegradable delivery medium.

The interior surfaces may define first and second reservoirs, each of which is configured to store a therapeutic agent delivery medium impregnated with a therapeutic agent. The elution channels may communicate the first and second reservoirs with the elution pores in series. The series arrangement of reservoirs prolongs elution as the therapeutic agent in one reservoir is preserved until the therapeutic agent is depleted or nearly depleted from the other reservoir.

BRIEF DESCRIPTION OF THE DRAWINGS

FIG. 1 is a perspective view of an implantable orthopedic device.

FIG. 2 is a sectional perspective view of a part of the device of FIG. 1.

FIG. 3 is a cross sectional view of the part shown in FIG. 2.

FIG. 4 is a perspective view of another implantable orthopedic device.

FIG. 5 is an opposite perspective view of the device shown in FIG. 4.

DETAILED DESCRIPTION

Figure 6:
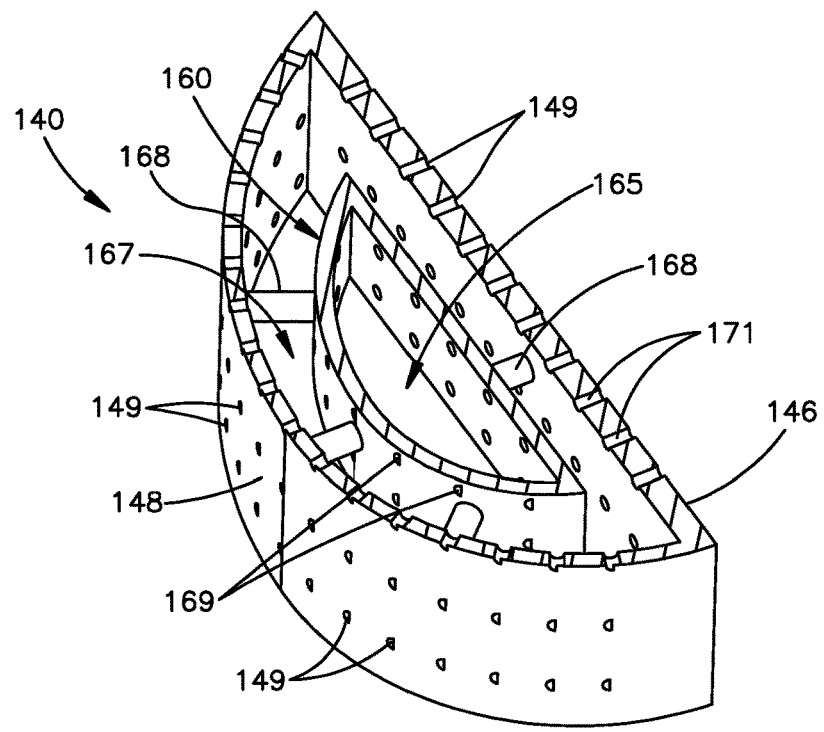
FIG. 6 is a perspective view of parts of the device shown in FIGS. 4 and 5.

The embodiments illustrated in the drawings have parts that are examples of the elements recited in the claims. The illustrated embodiments thus include examples of how a person of ordinary skill in the art can make and use the claimed invention. They are described here to meet the enablement and best mode requirements of the patent statute without imposing limitations that are not recited in the claims. One or more elements of one embodiment may be used in combination with, or as a substitute for, one or more elements of another as needed for any particular implementation of the invention.

A orthopedic implant device 10 is shown in FIG. 1. This example of an implant device 10 is a tibial component of a total knee replacement system. The device 10 thus includes an implant body 20 including a platform 22 and a stem 24. The platform 22 and the stem 24 are configured to provide elution of a therapeutic agent from within the body 20 over an extended period of time while the device 10 is implanted.

The platform 20 has a peripheral edge surface 30 providing a shape and thickness appropriate for implanting the platform 20 at the proximal end of a tibia. A proximal side surface 32 of the platform 20 serves as a bone-replacement surface, and in this example has a contour configured to replicate a proximal surface contour of a healthy tibial plateau. A distal side surface 34 has a contour configured to mate with the opposed contour of a tibial bone surface that has been surgically prepared to receive the device 10.

The stem 24 is configured for insertion into the medullary canal of the tibia to anchor the implanted device 10 in place. As best shown in FIG. 2, the stem 24 in the illustrated example has an elongated cylindrical shape with a longitudinal central axis 39, an open proximal end 40, and a closed distal end 42.

A major length section 44 of the stem 24 has a uniform outer diameter. The major length section 44 includes the distal end 42 of the stem 24. A minor length section 46 defines a cylindrical interior space 47, and includes the proximal end 40 of the stem 24. The minor length section 46 also has a reduced outer diameter above a shoulder surface 48. In this manner the minor length section 46 is shaped for fitting into a bore 49 that reaches through the platform 22 to support the stem 24 in the assembled position projecting distally from the platform 22, as shown in FIG. 1.

The major length section 44 of the stem 24 has an exterior surface 50 with pores 51. The major length section 44 further has interior surfaces defining reservoirs and channels in fluid flow communication with the pores 51. These include an innermost cylindrical surface 52 that is centered on the axis 39. The innermost surface 52 defines the length and diameter of a first reservoir 55 having a cylindrical shape reaching along the axis 39 between a closed distal end 56 and an open proximal end 58. A pair of radially opposed cylindrical inner surfaces 60 and 62 also are centered on the axis 39. These inner surfaces 60 and 62 together define the length and width of a second reservoir 65 having an annular shape that is spaced radially outward from, and surrounds, the first reservoir 55. The second reservoir 65 also has a closed distal end 70 and an open proximal end 72. Stiffeners 74 may reach radially across the second reservoir 65 for structural reinforcement.

Additional cylindrical inner surfaces define first and second channels 75 and 77. The first channels 75 reach radially outward from the first reservoir 55 to the second reservoir 65. The second channels 77 reach further outward from the second reservoir 65 to the pores 51. Construction of the reservoirs 55, 65, the channels 75, 77 and the pores 51 is preferably accomplished by an additive manufacturing process that forms the stem 24 as a single unitary body of agglomerated additive manufacturing material.

When the stem 24 is assembled with the platform 22 as shown in FIG. 1, the open proximal ends 58 and 72 of the reservoirs 55, 65 communicate with the bore 49 through the interior space 47 and the open proximal end 40 of the stem 24. Internal channels 81 in the platform 22 may provide fluid flow paths from the bore 49 to additional openings 83.

Before being implanted, the device 10 is charged with a solid therapeutic agent delivery medium. The delivery medium is impregnated with a drug or other therapeutic agent. This can be accomplished by forming a paste-like mixture of the therapeutic agent and a solid binder, and injecting the mixture into the reservoirs 55, 65 through the bore 49 and into the stem 24 through open proximal end 40.

For example, the therapeutic agent may comprise an antibiotic, such as gentamicin, and the solid binder may comprise a powdered material, such as calcium sulfate powder. A paste may be formed by mixing those ingredients with water. The injected paste will solidify within the reservoirs 55, 65, and will then permit gradual elution of the gentamicin outward through the channels 75, 77 from the reservoirs 55, 65 to the pores 51 as the calcium sulfate delivery medium biodegrades gradually under the influence of the patient's synovial fluid. This sustains the elution over a more extended period of time compared to the more rapid elution of a liquid in the absence of a solid binder.

In addition to the use of a solid binder, the arrangement of reservoirs 55, 65 and channels 75, 77 also contributes to the extended period of time taken for complete elution of the therapeutic agent. Specifically, the channels 75, 77 provide fluid flow communication between the reservoirs 55, 65 in series so that elution from the reservoirs 55, 66 proceeds sequentially rather than simultaneously. Elution is thus sustained as the therapeutic agent in the first reservoir 55 is preserved until the therapeutic agent is depleted or nearly depleted from the second reservoir 65.

Another example of an orthopedic implant device 100 is shown in FIGS. 4 and 5. In this example, the device 100 is a femoral component of a total knee replacement system. Like the device 10 described above, the device 100 is configured to provide elution of a therapeutic agent over an extended period of time.

The device 100 comprises an implant body 110 with medial and lateral legs 112 and 114 that are shaped as medial and lateral condyles. Accordingly, the medial leg 112 has an arcuate shape with a distal end portion 120. The exterior surface 122 at the distal end portion 120 serves as a bone-replacement surface with a contour configured to replicate a healthy medial condyle bone surface contour. The lateral leg 114 similarly has an arcuate shape with a distal end 124 portion at which the exterior surface 126 has a contour replicating a healthy lateral condyle bone surface contour. The distal end portions 120 and 124 are separated across a trochlear gap 125.

An intermediate section 140 of the body 110 reaches across the gap 125 between the medial and lateral legs 112 and 114. The intermediate body section 140 has planar opposite side surfaces 142. Each opposite side surface 142 has an arcuate anterior edge 144 adjoining the adjacent leg 112 or 114. A posterior surface 146 (FIG. 4) has a planar contour reaching across the intermediate body section 140 between the opposite side surfaces 142. An anterior surface 148 (FIG. 5) has an arcuate contour reaching along and across the gap 125 between the legs 112, 114. The posterior and anterior surfaces 146 and 148 each have an array of elution pores 149. In the illustrated example, the all of the elution pores 149 in the body 110 are remote from the bone replacement surface portions 122 and 126.

Figure 7:
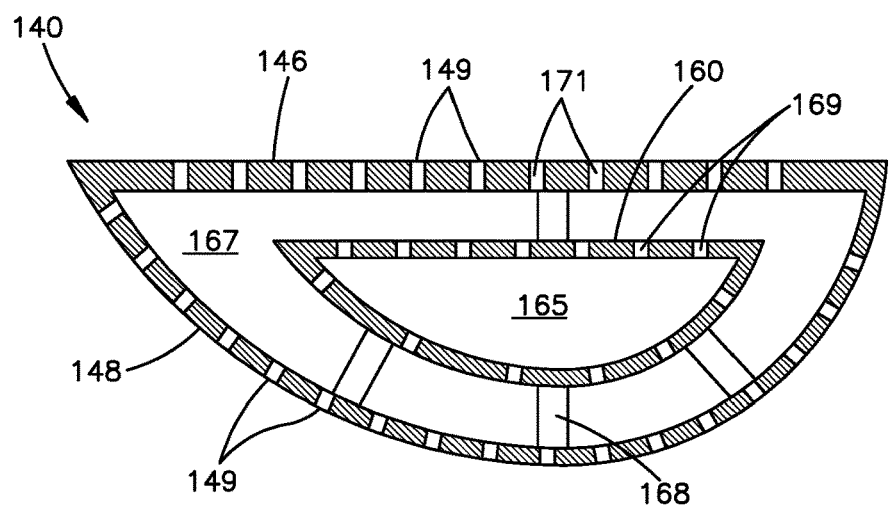
FIG. 7 is a section view of the parts shown in FIG. 6.

As shown separately in FIGS. 6 and 7, an internal wall structure 160 is located at the interior of the intermediate body portion 140. The internal wall structure 160 divides the interior of into first and second reservoirs 165 and 167. Stiffeners 168 may be provided for structural reinforcement, and the implant body 110 also may be defined by a single unitary body of agglomerated additive manufacturing material.

In use, each reservoir 165 and 167 in the implant body 110 stores a solid therapeutic agent delivery medium impregnated with a therapeutic agent, such as the solidified paste described above. One or more passages for injecting the paste into the reservoirs 165 and 167 can be provided in any suitable manner known in the art of additive manufacturing. Channels 169 reaching through the inner wall structure 160 communicate the first reservoir 165 with the second reservoir 167. Additional channels 171 communicate the second reservoir 167 with the pores 149 at the posterior and anterior external surfaces 146 and 148. The channels 169 and 171 connect the reservoirs 165 and 167 in series so that elution from the reservoirs 165 and 167 to the pores 149 proceeds sequentially rather than simultaneously, whereby elution is sustained as the therapeutic agent in the first reservoir 165 is preserved until the therapeutic agent is depleted or nearly depleted from the second reservoir 167.

This written description sets for the best mode of carrying out the invention, and describes the invention so as to enable a person of ordinary skill in the art to make and use the invention, by presenting examples of the elements recited in the claims. The detailed descriptions of those elements do not impose limitations that are not recited in the claims, either literally or under the doctrine of equivalents.

What is claimed is:

1. An orthopedic implant device comprising: a femoral implant body including: an exterior surface having medial and lateral condyle portions with contours configured to replicate healthy medial and lateral condyle bone surface contours, and further having elution pores; and interior surfaces defining a reservoir configured to store a solid therapeutic agent delivery medium impregnated with a therapeutic agent, and further defining elution channels communicating the reservoir with the elution pores to convey a therapeutic agent from the reservoir to the exterior surface; wherein the elution pores are located only between the medial and lateral condyle portions of the exterior surface.

2. An orthopedic implant device as defined in claim 1, wherein the exterior surface has anterior and posterior intermediate portions located laterally between the medial and lateral condyle portions, and the elution pores are located at the intermediate portions of the exterior surface.

3. An orthopedic implant device as defined in claim 2, wherein the anterior intermediate portion of the exterior surface has an arcuate contour.

4. An orthopedic implant device as defined in claim 2, wherein the posterior intermediate portion of the exterior surface has a planar contour.

5. An orthopedic implant device as defined in claim 1, further comprising a solid therapeutic agent delivery medium that is stored in the reservoir and is biodegradable under the influence of synovial fluid.

6. An orthopedic implant device as defined in claim 5, further comprising a therapeutic agent infused within the solid therapeutic agent delivery medium.

7. An orthopedic implant device comprising:
   an implant body including:
   an exterior surface having a bone-replacement portion with a contour configured to replicate a healthy bone surface contour, and further having elution pores; and
   interior surfaces defining first and second reservoirs that are spaced inward from the exterior surface and configured to store a solid therapeutic agent delivery medium impregnated with a therapeutic agent;

wherein the interior surfaces further define elution channels communicating the first and second reservoirs with the elution pores in series to convey a therapeutic agent outward from the first reservoir to the second reservoir, and further outward from the second reservoir to the exterior surface; and wherein the contour of the bone-replacement portion of the exterior surface is configured to replicate a healthy tibial bone surface contour.

8. An orthopedic implant device as defined in claim 7, wherein the second reservoir surrounds the first reservoir.

9. An orthopedic implant device as defined in claim 7, wherein the implant body includes an elongated stem with a longitudinal axis, the first reservoir is located within the stem, and the second reservoir is located within the stem radially outward of the first reservoir.

10. An orthopedic implant device as defined in claim 7, further comprising a solid therapeutic agent delivery medium that is stored in the first and second reservoirs, is biodegradable under the influence of synovial fluid, and is impregnated with a therapeutic agent.

11. An orthopedic implant device as defined in claim 7 wherein the reservoirs, channels and pores are defined by a continuous body of agglomerated additive manufacturing material.

12. An orthopedic implant system comprising:
a) a femoral implant body including:
an exterior surface having medial and lateral condyle surface portions with contours configured to replicate healthy medial and lateral condyle bone surface contours, and further having femoral elution pores; and interior surfaces defining a femoral reservoir configured to store a solid therapeutic agent delivery medium impregnated with a therapeutic agent, and further defining elution channels communicating the femoral reservoir with the femoral elution pores to convey a therapeutic agent from the femoral reservoir to the exterior surface of the femoral implant body;

wherein the femoral reservoir is located laterally between the medial and lateral condyle surface portions; and b) a tibial implant body including:
an exterior surface having a bone-replacement portion with a contour configured to replicate a healthy bone surface contour, and further having tibial elution pores; and interior surfaces defining first and second tibial reservoirs that are spaced inward from the exterior surface of the tibial implant body and configured to store a solid therapeutic agent delivery medium impregnated with a therapeutic agent;

wherein the interior surfaces of the tibial implant body further define elution channels communicating the first and second tibial reservoirs with the tibial elution pores in series to convey a therapeutic agent outward from the first tibial reservoir to the second tibial reservoir, and further outward from the second tibial reservoir to the exterior surface of the tibial implant body; and wherein the contour of the bone-replacement portion of the exterior surface of the tibial implant body is configured to replicate a healthy tibial bone surface contour.

13. An orthopedic implant system as defined in claim 12, wherein the exterior surface of the femoral implant body has anterior and posterior intermediate surface portions located laterally between the medial and lateral condyle surface portions, and the femoral elution pores are located at the intermediate surface portions.

14. An orthopedic implant system as defined in claim 13, wherein the anterior intermediate surface portion has an arcuate contour.

15. An orthopedic implant system as defined in claim 13, wherein the posterior intermediate surface portion has a planar contour.

16. An orthopedic implant system as defined in claim 12, wherein the medial and lateral condyle surface portions are both free of elution pores communicating with the femoral reservoir.

17. An orthopedic implant system as defined in claim 12, wherein the second tibial reservoir surrounds the first tibial reservoir.

18. An orthopedic implant system as defined in claim 12, wherein the tibial implant body includes an elongated stem with a longitudinal axis, the first tibial reservoir is located within the stem, and the second tibial reservoir is located within the stem radially outward of the first tibial reservoir.

19. An orthopedic implant system as defined in claim 12, further comprising a solid therapeutic agent delivery medium that is stored in the femoral reservoir and the first and second tbial reservoirs, wherein the solid therapeutic agent delivery medium is biodegradable under the influence of synovial fluid and is impregnated with a therapeutic agent.

* * * * *